(12) United States Patent
Kappler et al.

(10) Patent No.: US 10,674,991 B2
(45) Date of Patent: Jun. 9, 2020

(54) METHOD FOR CALIBRATING AN X-RAY MEASURING FACILITY

(71) Applicant: Siemens Healthcare GmbH, Erlangen (DE)

(72) Inventors: Steffen Kappler, Effeltrich (DE); Achim Hillenbrand, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/210,051

(22) Filed: Dec. 5, 2018

(65) Prior Publication Data
US 2019/0175137 A1 Jun. 13, 2019

(30) Foreign Application Priority Data
Dec. 11, 2017 (EP) .................................... 17206434

(51) Int. Cl.
*A61B 6/00* (2006.01)
*A61B 6/03* (2006.01)
*G01N 23/046* (2018.01)
*G01T 1/29* (2006.01)
*G01T 7/00* (2006.01)

(52) U.S. Cl.
CPC ............. *A61B 6/584* (2013.01); *A61B 6/032* (2013.01); *A61B 6/4241* (2013.01); *A61B 6/482* (2013.01); *A61B 6/583* (2013.01); *A61B 6/585* (2013.01); *G01N 23/046* (2013.01); *G01T 1/2985* (2013.01); *G01N 2223/3035* (2013.01); *G01N 2223/423* (2013.01); *G01T 7/005* (2013.01)

(58) Field of Classification Search
None
See application file for complete search history.

(56) References Cited

U.S. PATENT DOCUMENTS

2008/0137803 A1* 6/2008 Wu ........................ A61B 6/032
378/5
2016/0022243 A1* 1/2016 Nakai .................... A61B 6/483
378/5
(Continued)

OTHER PUBLICATIONS

European Search Report for European Application No. EP17206434, dated Jun. 26, 2018.

*Primary Examiner* — Hoon K Song
(74) *Attorney, Agent, or Firm* — Harness, Dickey & Pierce, P.L.C.

(57) ABSTRACT

A method is for calibrating an X-ray measuring facility. The method includes preparing the facility for measurement for a resolution of a plurality of different energy intervals; positioning a test object in a beam path of an X-ray beam; irradiating the test object via the X-ray beam, and during the irradiating, an intensity measurement of the test object appropriately resolved according to the energy intervals is carried out by the facility; determining an absorption function of the test object using the intensity measurement; preparing one of the energy intervals as a reference interval such that the absorption function has a negligible energy dependency over the reference interval; determining a correction function of the absorption function, for at least one further energy interval of the energy intervals, using at least one value of the absorption function in the reference interval; and calibrating the facility using the correction function determined.

18 Claims, 3 Drawing Sheets

(56) References Cited

U.S. PATENT DOCUMENTS

2016/0033654 A1    2/2016   Tamura et al.
2017/0258412 A1    9/2017   Daerr et al.
2018/0270939 A1*   9/2018   Proksa .................... A61B 6/40

* cited by examiner

METHOD FOR CALIBRATING AN X-RAY MEASURING FACILITY

PRIORITY STATEMENT

The present application hereby claims priority under 35 U.S.C. § 119 to European patent application number EP17206434.7 filed Dec. 11, 2017, the entire contents of which are hereby incorporated herein by reference.

FIELD

Embodiments of the invention generally relate to a method for calibrating an X-ray measuring facility which comprises a spectrally sensitive X-ray detector, wherein a test object is positioned in the beam path of an X-ray beam, the test object is irradiated by the X-ray beam, and in the process an intensity measurement of the test object is carried out by way of the X-ray measuring facility, and an absorption function of the test object is determined from the intensity measurement of the test object, wherein a correction function of the absorption function is determined, and the X-ray measuring facility is calibrated using the correction function.

BACKGROUND

In a computer tomograph (CT), various absorption profiles of the body tissue to be examined are recorded by X-ray beams which are emitted from different angular directions around and onto a patient body, and a volume model of the body tissue is reconstructed using this absorption profile and knowledge of the beam path used. Before the CT is commissioned, or even at periodic intervals, such as, for example during scheduled maintenance works, the X-ray measuring facility of the CT is calibrated in order to be able to generally correct errors in the image, which errors can occur owing to the measuring apparatus or owing to the measuring principle used.

One of the effects to be considered during calibration is what is known as beam hardening, which occurs when using polychromatic X-ray spectra, and this can lead to image artifacts (what are known as "cupping artifacts"). Beam hardening is based on the physical principle that the absorption is energy-dependent, so in the X-ray spectrum, high-energy photons of human tissue or material having similar optical properties are absorbed to a lesser extent than X-ray photons with lower energy. During propagation of the X-ray radiation through an object, such as a test body made of water or through a human body, the X-ray spectrum striking the X-ray detector therefore has a transmitted spectrum with a higher energy mean than the input spectrum owing to the stronger absorption of the low-energy components.

This beam hardening can now accordingly lead to a falsification of the absorption profiles as a function of the thickness of the body tissue examined in the respective absorption profile. In particular, a volume element of the material in the interior of a relatively large object has an apparently lower absorption coefficient than a comparable volume element at the surface of the object. During three-dimensional reconstruction artifacts can consequently occur in which, in particular, a homogenous object can be displayed by the CT as inhomogeneous.

Often the absorption profiles of test bodies of known geometry, and in particular known thickness, are therefore measured for a correction, and correction functions created herefrom for the absorption data generated by the X-ray detector. However, this means a considerable amount of effort when calculating the correction function since a relatively large number of test bodies is often required or a satisfactory correction of the beam hardening.

SUMMARY

A method of at least one embodiment is for calibrating an X-ray measuring facility, which is capable of correcting the potential effects of beam hardening on the measuring results of the X-ray measuring facility with optimally low effort.

At least one embodiment of the invention is directed to a method for calibrating an X-ray measuring facility which comprises a spectrally sensitive X-ray detector, wherein the X-ray measuring facility is prepared for measurement for a resolution of a plurality of different energy intervals, a test object is positioned in the beam path of an X-ray beam, the test object is irradiated by the X-ray beam, in particular from different angles and in different positions, and in the process an intensity measurement of the test object appropriately resolved according to the energy intervals is carried out by way of the X-ray measuring facility, and an absorption function of the test object is determined using the intensity measurement of the test object. It is provided in this connection that one of the energy intervals is used or is prepared as a reference interval in such a way that the absorption function has a negligible energy dependency over the reference interval, that a correction function of the absorption function is determined for at least one further energy interval using at least one value of the absorption function in the reference interval, and that the X-ray measuring facility is calibrated using the correction function.

At least one embodiment of the invention is directed to a method for calibrating an X-ray measuring facility including a spectrally sensitive X-ray detector, the method comprising:

preparing the X-ray measuring facility for measurement for a resolution of a plurality of different energy intervals;

positioning a test object in a beam path of an X-ray beam;

irradiating the test object via the X-ray beam, and during the irradiating, an intensity measurement of the test object appropriately resolved according to the plurality of different energy intervals is carried out by the X-ray measuring facility;

determining an absorption function of the test object using the intensity measurement of the test object;

preparing one of the plurality of different energy intervals as a reference interval such that the absorption function has a negligible energy dependency over the reference interval;

determining a correction function of the absorption function, for at least one further energy interval of the plurality of different energy intervals, using at least one value of the absorption function in the reference interval; and calibrating the X-ray measuring facility using the correction function determined.

At least one embodiment of the invention also cites an imaging medical device having at least one X-ray source for generating an X-ray beam as well as an X-ray measuring facility which is adapted for calibrating the X-ray measuring facility according to an embodiment of the method. The advantages disclosed for embodiments of the method for calibrating and for its developments can analogously be transferred to the imaging medical device.

At least one embodiment of the invention is directed to an imaging medical device, comprising:

at least one X-ray source to generate an X-ray beam; and an X-ray measuring facility, the X-ray measuring facility being configured to be calibrated by preparing the X-ray measuring facility for measurement for a resolution of a plurality of different energy intervals;

positioning a test object in a beam path of an X-ray beam;

irradiating the test object via the X-ray beam, and during the irradiating, an intensity measurement of the test object appropriately resolved according to the plurality of different energy intervals is carried out by the X-ray measuring facility;

determining an absorption function of the test object using the intensity measurement of the test object;

preparing one of the plurality of different energy intervals as a reference interval such that the absorption function has a negligible energy dependency over the reference interval;

determining a correction function of the absorption function, for at least one further energy interval of the plurality of different energy intervals, using at least one value of the absorption function in the reference interval; and calibrating the X-ray measuring facility using the correction function determined.

BRIEF DESCRIPTION OF THE DRAWINGS

An example embodiment of the invention will be illustrated in more detail below with reference to a drawing. Here, in each case schematically.

Mutually corresponding parts and variables are provided with identical reference numerals in all figures respectively.

DETAILED DESCRIPTION OF THE EXAMPLE EMBODIMENTS

Figure 1:
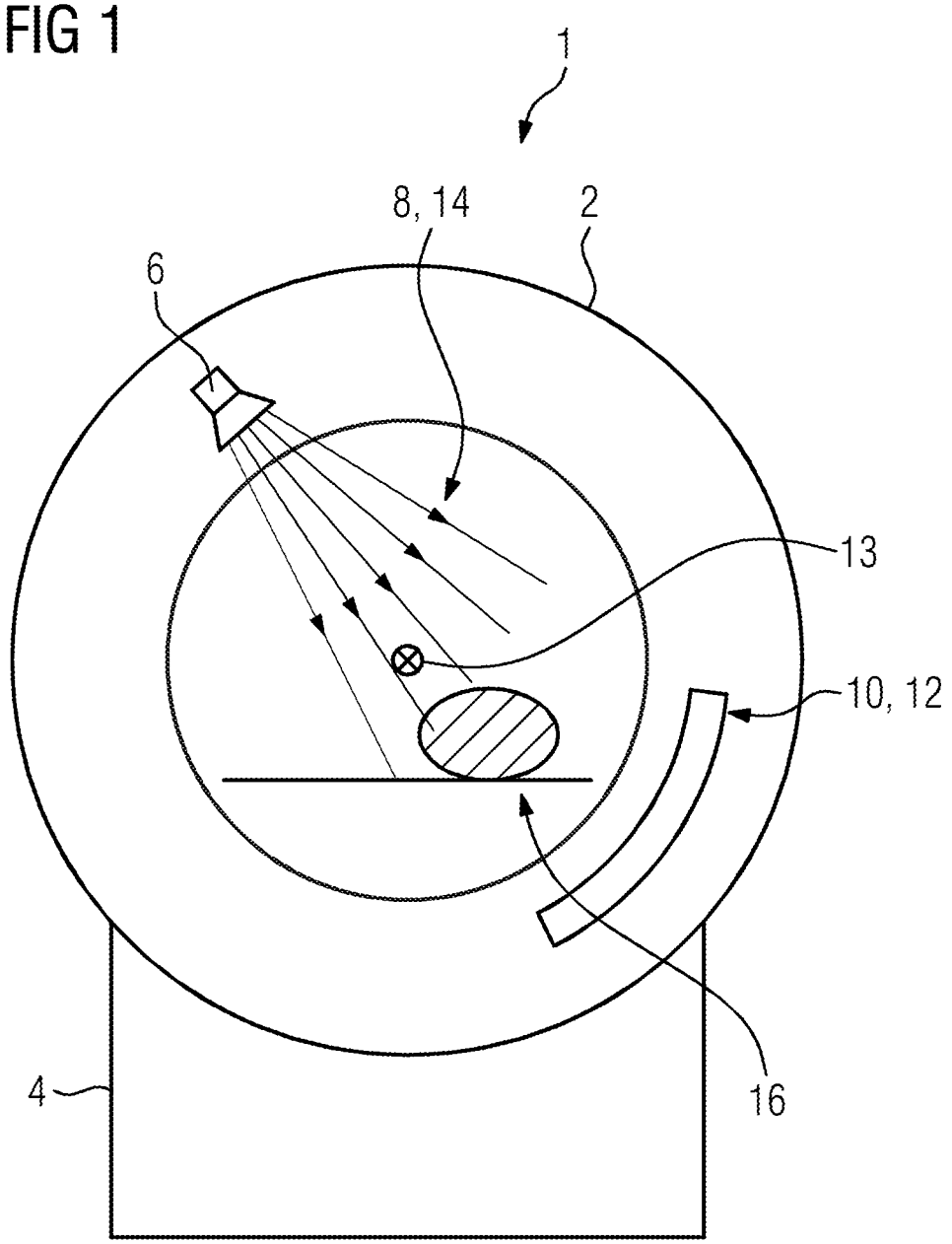
FIG. 1 shows in a cross-section a CT in which a test body for calibrating an X-ray detector is positioned.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

At least one embodiment of the invention is directed to a method for calibrating an X-ray measuring facility which comprises a spectrally sensitive X-ray detector, wherein the X-ray measuring facility is prepared for measurement for a resolution of a plurality of different energy intervals, a test object is positioned in the beam path of an X-ray beam, the test object is irradiated by the X-ray beam, in particular from different angles and in different positions, and in the process an intensity measurement of the test object appropriately resolved according to the energy intervals is carried out by way of the X-ray measuring facility, and an absorption function of the test object is determined using the intensity measurement of the test object. It is provided in this connection that one of the energy intervals is used or is prepared as a reference interval in such a way that the absorption function has a negligible energy dependency over the reference interval, that a correction function of the absorption function is determined for at least one further energy interval using at least one value of the absorption function in the reference interval, and that the X-ray measuring facility is calibrated using the correction function.

Advantageous embodiments and those that are partly inventive when taken alone are the subject of the claims and the description below.

In particular, the X-ray measuring facility is arranged in a CT, or provided for intended operation in a CT and adapted accordingly. Preparation of the X-ray measuring facility for measurement for a resolution of a plurality of different energy intervals comprises, in particular, that measurements are made which make it possible by way of the X-ray measuring facility with one-time irradiation of the test body by the X-ray beam, to be able to register a resulting intensity profile with the corresponding energy resolution, and to therefore preferably individually obtain a separate intensity profile for each energy interval of the X-ray radiation. In particular, the intensity measurement appropriately resolved according to the energy intervals is implemented as a measurement in which a separate, preferably spatially resolved, intensity profile is therefore individually generated for each energy interval of the X-ray radiation.

Here, a test object is in particular a body having known geometric dimensions and having known material properties in its interior in respect of the manner and the spatial distribution which preferably has certain geometric regularity and in particular a convexity.

A reference intensity measurement of the X-ray beam appropriately resolved according to the energy intervals is preferably carried out by way of the X-ray measuring facility, with the absorption function of the test object also being determined using the reference intensity measurement of the X-ray beam.

The maximum intensity $I_0$ is particularly preferably measured here, and this is achieved if the X-ray beam irradiates the X-ray measuring facility without any absorbing objects in its beam path. $I_0$ is therefore the reference intensity in respect of air. The transmitted intensity I of the test object is then measured, and an absorption function a is determined herefrom, for example as the logarithmic ratio of the intensity transmitted by the test object based on the reference intensity $I_0$, in other words $a=-\log(I/I_0)$. Other mathematical definitions are also conceivable for the absorption function a, however, provided these are firstly monotonous in the intensity measurement, and, secondly, consistently have a counter monotony in the reference intensity $I_0$, and meet the standard condition $a=0$ for $I=I_0$, which takes account of the fact that there is no absorption if the measured intensity is equal to the reference intensity.

The relevant energy interval can be prepared as a reference interval in particular on the basis of theoretical knowledge and considerations in respect of the absorption function $a\grave{}$ to be expected in a measurement. Therefore, an absorption function a+ can be obtained for the test body or for a comparison test body, which has similar geometric and material properties, for example from comparison measurements highly resolved in the energy space and for the test body an expected absorption function $a\grave{}$ can be determined from a measurement, which is comparable with the measurements in the method, using a transfer of the obtained measuring result and the knowledge drawn herefrom to the test body.

From an energy dependency of the expected absorption function $a\grave{}$, firstly the value range im(E) can now be determined as a function of the energy E, so a reduced value range $im_R(E)$ can be determined herefrom which represents a negligible energy dependency for the corresponding energy of the incident photons, so for example $$da\grave{}/dE \sim 0 \text{ for E from } im_R(E)$$

applies. Furthermore, the corresponding energy range $\Delta E_R$ can also be determined in the energy space, for which range the expected absorption function $a\grave{}$ assumes values in this reduced value range $im_R(E)$. Therefore, the energy dependency of the expected absorption function $a\grave{}$ in the framework of the present orders of magnitude, which are given by the value range im(E), is negligible over the energy range $\Delta E_R$ determined in this way. The behavior determined using the expected absorption function $a\grave{}$ is now transferred to the real measurements in the method, and the determined energy range $\Delta E_R$ is prepared in particular as the reference interval.

Here, determining a correction function of the absorption function for at least one further energy interval using at least one value of the absorption function in the reference interval should in particular be taken to mean that, firstly, at least one value of the absorption function is determined, which corresponds to an energy of the incident X-ray photons in the reference interval. A plurality of values of this kind is preferably determined. Using this/these value(s), a correction function of the absorption function a is then determined depending thereon for the entire energy range, by which correction function the measured values of the absorption function a, in particular outside of the reference interval $im_R(E)$, are to be corrected.

Owing to the energy dependency of the absorption function a that is negligible per construction over the reference interval $im_R(E)$, the totality of the values of the absorption function a ($\Delta E_R$) for the reference interval $\Delta E_R$ corresponds to an essentially monochromatic X-ray beam, even if the spectral width of the incident X-ray radiation is actually still finite since this occurs in a frequency or energy range in which the finiteness of the spectral width does not have any notable effects on the absorption function a. This means that an X-ray beam is filtered by way of the corresponding preparation of the X-ray measuring facility in respect of the reference interval in such a way that it has the same effect in the reference interval $\Delta E_R$ on the behavior of the absorption function a as a monochromatic X-ray beam.

Owing to the energy dependency of the absorption of X-ray photons in a material, the intensity of a monochromatic X-ray beam transmitted through a test body or its absorption is, however, only characterized by an exponential attenuation, and this depends solely on the thickness of the material to be penetrated by the X-ray beam. This exponential attenuation can vary in its penetration depth for different materials. In other words, a material-dependent pre-factor in relation to the thickness also occurs in the exponent as the actual variable, although the functional dependency is clearly predefined here. This relationship for monochromatic X-ray photons is preferably adequately taken into account by the definition of the absorption function a, as, for example, in that given above by the logarithm of the intensities, so the absorption function a depends linearly on the thickness in this case.

The correction function can be specifically determined in such a way that for each spatial resolution pixel of the X-ray measuring facility, the measured intensities for different measurements of the test body, preferably each having different thicknesses of the penetrated material of the test body, are plotted in what is known as a scatter plot in which, for example, the abscissa value is the measured absorption function a, while the ordinate value is given by the absorption function A (not to be confused with the expected absorption function a` when determining the monotony behavior of the absorption function a) assumed in the case of the corresponding thickness for a monochromatic X-ray beam. From the points or value pairs in the scatter plot that are generated in this way, a correction function of the absorption function a can now be determined depending thereon in such a way that the corrected absorption function A(a) matches that which would be obtained for monochromatic X-ray photons. The correction function can be determined from said points or value pairs in the scatter plot by way of methods known in statistical data processing, for example by means of a polynomial smoothing.

Using the correction function or the corrected absorption function A(a), the X-ray measuring facility can now be calibrated in such a way that effects of beam hardening are corrected, and in particular the Hounsfield scale can be adhered to unrestrictedly for standardizing.

In an advantageous embodiment of the invention a broadband energy interval is prepared as the reference interval, whose lower limit has at least the value of 60%, preferably at least ⅔ of the maximum energy of the spectrum of the X-ray beam, and whose spectral width preferably has at least ⅕, particularly preferably at least ¼ of the maximum energy of the spectrum of the X-ray beam. The maximum energy of the spectrum of the X-ray beam is limited in particular here by the acceleration voltage of the anode of the X-ray tubes generating the X-ray radiation.

Such a process takes account firstly of the fact that conventional X-ray measuring facilities, such as, for example quantum-counting X-ray detectors, usually have only a finite resolution in the energy space in the extent of for example four to six energy intervals and therefore in the state adapted for intended operation in view of the X-ray spectrum of approx. 10 keV to well over 100 keV, each have a significant spectral width. Secondly, use is made here of the fact that already no further significant beam hardening takes place during transmission or absorption in the test body or in the patient tissue for the high-energy X-ray photons in the stated spectral range, and therefore the absorption function in this range no longer exhibits a significant energy dependency, so the entire broadband energy interval can be used as a reference interval.

An energy interval provided for energy-resolved normal operation of the X-ray measuring facility is advantageously selected as the reference interval in this case. This has the advantage that the individual energy intervals can equally be prepared for the measurements for determining the correction function in the framework of a preparation for commissioning.

In a further advantageous embodiment of the invention a narrowband energy interval is prepared as the reference interval, whose spectral width is at most ⅛, preferably at most ¹⁄₁₀ of the maximum energy of the spectrum of the X-ray beam. This means in particular that a corresponding energy interval is prepared separately as the reference interval for the measurements for determining the correction function, by which reference interval the correction function for the other energy intervals, as are provided for energy-resolved normal operation of the X-ray measuring facility, are determined for corresponding calibration. Measurements for a plurality of reference intervals of comparable spectral width and different positioning in the energy range are preferably carried out to obtain a particularly good energy resolution and a high level of precision in the energy space for the entire X-ray spectrum.

Preparation of the reference interval is expediently suspended for energy-resolved normal operation of the X-ray measuring facility. In other words, following the measurements for determining the correction function and a corresponding calibration of the individual energy intervals of the X-ray measuring facility for energy-resolved normal operation, the reference interval can no longer be found in the configuration of the energy intervals.

It has also proven to be advantageous if values of the absorption function for the reference interval are plotted in a spatially resolved manner against values of the absorption function for the at least one further energy interval, and, from this, the absorption function for the reference interval is determined in the relevant energy interval, depending on the absorption function A(a) for the at least one further energy interval, as a correction function. In particular, this means that each spatial resolution pixel of the X-ray measuring facility is appropriately plotted. This can occur in particular in the form of a scatter plot, wherein the correction function can be determined using statistical methods, such as, for example polynomial smoothing, from the data generated in this way. In this way, a functional relationship can be established particularly easily between the measurements in the various energy intervals actually determined by the X-ray measuring facility and a hypothetical measurement for monochromatic X-ray radiation, and this functional relationship can then be used for the correction.

In a further advantageous embodiment the X-ray measuring facility performs a rotational movement in respect of the test object for the intensity measurement of the test object. In particular, the radiation source of the X-ray beam also performs a rotation, and the two rotations are preferably synchronized with each other in such a way that the X-ray measuring facility and X-ray beam source do not move relative to each other. In particular, the path length, which the X-ray beam propagates through the test object, is varied here by the rotation. Using knowledge of this path length, by means of just one test object it is possible to obtain values of the absorption function for various thicknesses of the test object without having to carry out laborious positioning of a plurality of test objects for this purpose. In a CT this is particularly advantageous owing to the need for reconstruction of the volume model from the absorption or intensity data and a correspondingly necessary calibration by way of various thicknesses of the test object.

A quantum-counting X-ray detector is advantageously calibrated as the X-ray measuring facility. An X-ray detector of this kind allows energy-resolved detection of X-ray photons with high spatial resolution, with complex calibration being necessary, however, for correct standardization of the counting events in respect of the reference intensity I0 without object in the beam path, for which calibration the proposed method is particularly suitable.

It has also proven to be advantageous if the reference interval is prepared by way of at least one voltage level in a signal amplifier of the X-ray measuring facility. The spatially resolved detection of X-ray photons can occur in different ways. One possibility in this case is, in general, to convert the energy of the incident X-ray photons by ionizing atoms in a crystal provided for this purpose, for example a semiconductor, into electrical charges and further into current or voltage signals. The amplitude of the corresponding current or voltage signal is preferably proportional to the energy of an incident X-ray photon in each case. Filtering in the detector according to individual energy ranges can then occur using said voltage steps, for example within the meaning of "bias voltages", against which the generated current or voltage signal has to run, so the signals from X-ray photons with lower energy than that corresponding to the selected bias voltage do not overcome the bias voltage, and therefore the signal is not registered accordingly. Therefore the energy range can be divided into a plurality of intervals by way of a plurality of voltage steps.

At least one embodiment of the invention also cites an imaging medical device having at least one X-ray source for generating an X-ray beam as well as an X-ray measuring facility which is adapted for calibrating the X-ray measuring facility according to an embodiment of the method. The advantages disclosed for embodiments of the method for calibrating and for its developments can analogously be transferred to the imaging medical device.

The described method is advantageous in particular for an imaging medical device in which a spectrally sensitive X-ray detector is used for 3D reconstruction. The imaging medical device can therefore be designed in particular as a CT, but also as a C-arm device.

FIG. 1 schematically shows in a cross-section a CT 1 which has a rotating assembly 2 and a holding frame 4. A X-ray source 6 for generating an X-ray beam 8 and an X-ray measuring facility 10, which is designed as a quantum-counting X-ray detector 12, are arranged on the rotating assembly 2. During operation of the CT 1 the rotating assembly 2 accordingly rotates about an axis 13 perpendicular to the image plane, wherein a patient positioned in the interior of the rotating assembly 2 is penetrated by the X-ray beam 8 from different angular directions, so a two-dimensional absorption profile of the X-ray radiation is generated by the X-ray detector 12 for each of these angular directions, which profile is transmitted to an image processing unit (not shown) on the holding frame 4. A three-dimensional volume model of the patient tissue examined in the CT is then generated by way of a back transformation from the totality of the absorption profiles generated for all angular directions.

Owing to the energy dependency of the absorption of X-ray radiation by all types of body tissue and also water, and the resulting beam hardening, in other words the shifting of the X-ray spectrum due to an object positioned in the beam path 14 of the X-ray beam 8 through to, on average, high-energy X-ray photons, the individual absorption profiles should be corrected here in respect of the beam hardening so the actually determined absorption for one angular direction does not contain any distortions caused by the thickness of the absorbing tissue. Calibration measurements of the absorption profiles of a plurality of test objects of known geometry and material characteristics are conventionally carried out for a correction of this kind in order to obtain additional information in respect of an expected absorption distribution using knowledge of the thickness of the penetrated test object for one angular direction.

In the present case a different path is now being proposed which requires only the measurement of a single test object 16, as is described with reference to the following figures.

Figure 2:
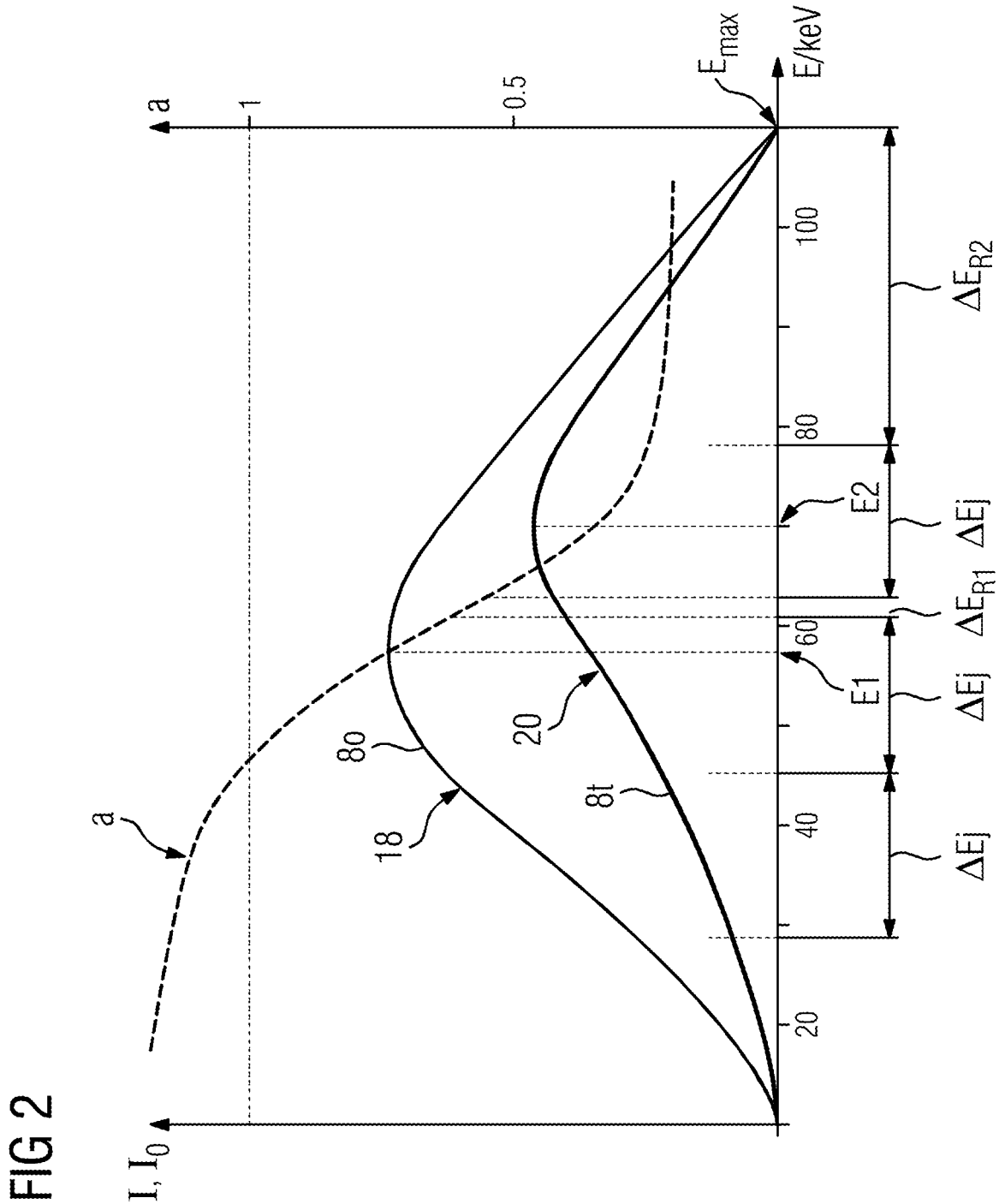
FIG. 2 shows in a graph for a pixel of the X-ray detector in FIG. 1 a reference intensity measurement and a measurement of the intensity transmitted by the test body.

FIG. 2 schematically shows in a graph the intensity I0 of an X-ray beam 8o without filtering through a test object and the intensity I of an X-ray beam 8t partially absorbed by a test object 16 in FIG. 1 for a pixel of the X-ray detector 12 against the energy E of the incident X-ray photons. The values for the individual energy levels decisively depend on the anode material of the X-ray source used. For the sake of clarity, a depiction of the spectral contributions of the line spectrum characteristic of the anode material has been omitted here.

The intensity I0 of the unfiltered X-ray beam 8o firstly has a monotonous increase 18 in energy E in order to assume its maximum with an energy E1 of just over 55 keV and to then decrease monotonously. Owing to the higher level of absorption with lower energy levels, the intensity I of the X-ray beam 8t filtered by the test object 16 initially has a much flatter increase 20 in order to then assume the maximum with a value E2 of approx. 70 keV. It also becomes clear from the graph in FIG. 2 that the fundamental contributions of the intensity I for the X-ray beam 8t are shifted, generally starting from the intensity I0 of the X-ray beam 8o, in the direction of higher energy levels.

For the sake of better illustration, FIG. 2 also indicates the energy-resolved detection, as is detected and passed on by the X-ray detector 12 in FIG. 1. The X-ray detector divides the energy E into individual energy intervals $\Delta E_j$. All X-ray photons, whose energy lies in such an energy interval $\Delta E_j$, consequently have the same energy for the X-ray detector 12 in the context of its energetic resolution capacity, and this is accurately given by the energy intervals $\Delta E_j$. The intensities I, I$_0$ are then only detected as blocks $I(\Delta E_j)$, $I_0(\Delta E_j)$ that are not illustrated in the present case.

An absorption function $a := -\log(I/I_0)$, marked as broken lines with scaling on the right-hand axis, obviously owing to the energy dependency of the involved intensities I, I$_0$, for its part now has a corresponding energy dependency. Correct detection of the energy dependency in the absorption function a would be lost due to the rough division of the energy into individual intervals $\Delta E_j$ if this energy dependency of the absorption function a, as is the case here for calibrating of the X-ray detector 12, is relevant and cannot be ignored.

However, an energy interval $\Delta E_{R1}$ is selected to be so narrow—in this case from 60 to 62 keV—that the absorption function a $\Delta E_{R1}$ changes only by approx. 0.05 with a value range of approx. 0.2 to approx. 1.2, in other words negligibly, over said energy interval $\Delta E_{R1}$. For this energy interval $\Delta E_{R1}$ the X-ray beam 8 is therefore essentially monochromatic in respect of the behavior of the absorption function a, so it can be used as a reference interval with measurements in which knowledge of the absorption function is desired for a monochromatic X-ray beam.

Depending on the application, the energy interval $\Delta E_{R1}$ can also be selected to be wider, however, with the selection depending on the behavior of the absorption function a. Therefore, in view, for example, of the maximum energy $E_{max}$ of the spectrum of the X-ray beam 8 of approx. 110 keV, the reference interval $\Delta E_{R1}$ over the range of approx. 70-80 keV can also be selected with a spectral width of approx. 10-11 keV since there the absorption function a changes its values only insignificantly compared to the overall value range.

One further possibility for an energy interval without significant energy dependency of the absorption function a, and therefore one further possibility of a reference interval, is given by the energy interval $\Delta E_{R2}$ at the high-energy margin of the spectrum. Here the energy interval $\Delta E_{R2}$ has a considerable spectral width of several tens of keV, but this spectral width is of no real consequence owing to the behavior of the two intensities I, I$_0$ during the course of the absorption function a, for which reason the energy interval $\Delta E_{R2}$ can also be used as a reference interval.

Figure 3:
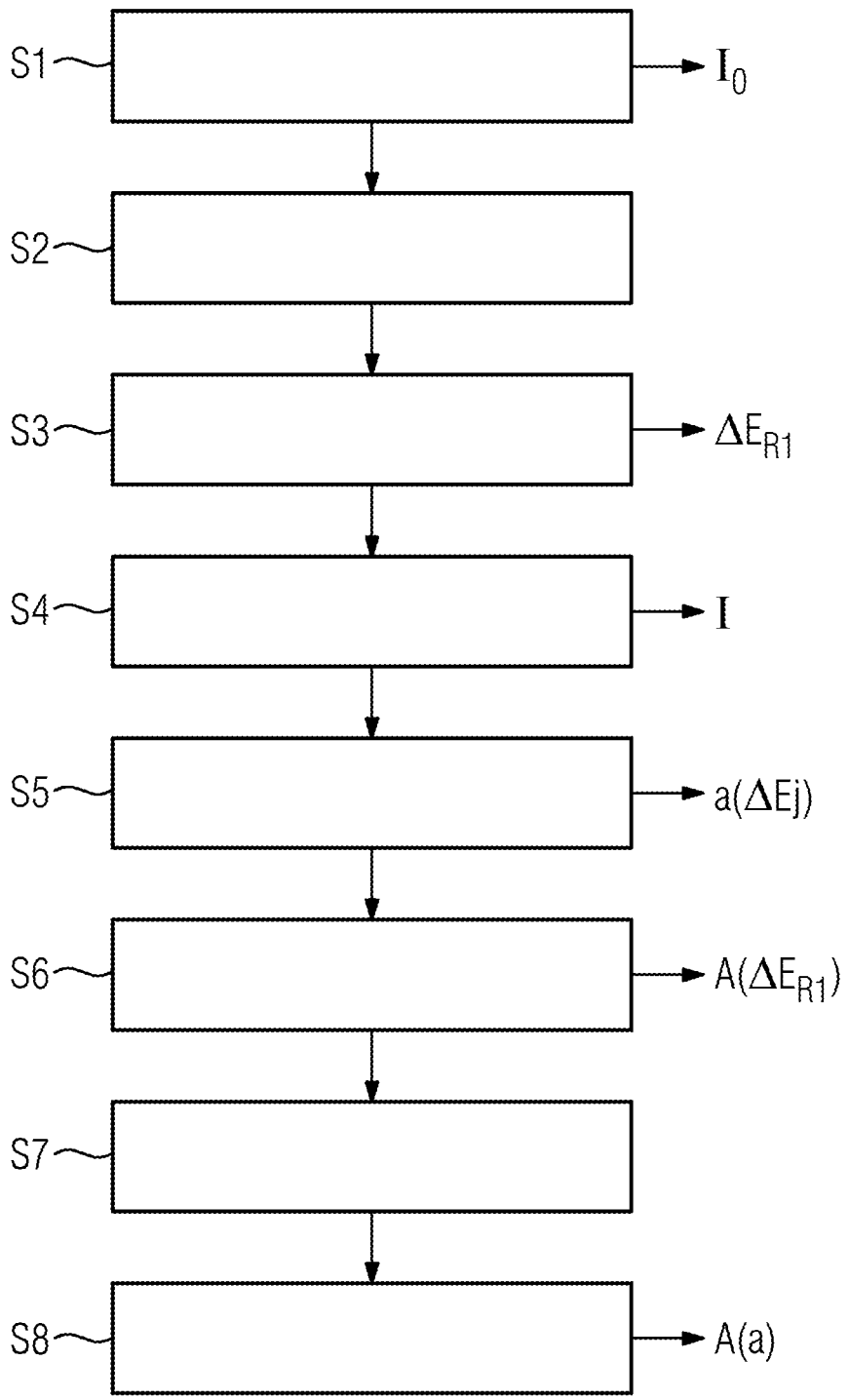
FIG. 3 shows in a block diagram a method for calibrating the X-ray detector in FIG. 1.

This knowledge can now be used to determine a correction function for the absorption function actually measured during operation. Using a block diagram, FIG. 3 schematically shows in this respect the course of a method for calibrating the X-ray detector 12 of the CT 1 in FIG. 1. A reference measurement of the intensity $I_0$ of the X-ray beam 8 filtered only by the air in the interior of the CT is carried out in a first step S1. Next, the test object 16 is positioned in the beam path 14 of the X-ray beam 8 in a step S2. The test object should preferably be eccentrically supported for this, so X-ray beams 8t generated for different angular directions have to cover a different path length through the test object 16, and this can be considered when calculating the correction function.

In the next step S3 an energy interval $\Delta E_j$ is prepared as the reference interval $\Delta E_{R1}$ by adjusting appropriate voltage steps in the pre-amplification for the generated signal. A narrowband energy interval is selected in the present case. In the following step S4 a measurement of the intensity I of the X-ray beam 8t transmitted by test object 16 is carried out in a spatially resolved manner and the prepared energy intervals, including the reference interval $\Delta E_{R1}$, are measured in an energy-resolved manner accordingly. Values of an absorption function a for each energy interval $\Delta E_j$ to be calibrated are now calculated in a step S5 from the reference intensity $I_0$ and the intensity I transmitted by test object 16. In addition, the values of the absorption function A are calculated in the next step S6 for the reference interval $\Delta E_{R1}$. A scatter plot is then produced in a step S7 for each energy interval $\Delta E_j$ and each pixel of the X-ray detector 12, with the values a of the measured absorption function in the energy interval $\Delta E_j$ to be calibrated being marked on the abscissa axis, and the values A of the reference interval $\Delta E_{R1}$ on the ordinate axis. A function A(a) is then determined in a step S8 from the values of the set of points, which for the relevant pixel produces the correction function for correction of the beam hardening in the corresponding energy interval $\Delta E_j$ and hereby calibrates the X-ray detector.

Although the invention has been illustrated and described in detail by the preferred example embodiment, it is not limited by this example embodiment. A person skilled in the art can derive other variations herefrom without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for calibrating an X-ray measuring facility including a spectrally sensitive X-ray detector, the method comprising:
   preparing the X-ray measuring facility for measurement for a resolution of a plurality of different energy intervals;
   positioning a test object in a beam path of an X-ray beam;
   irradiating the test object via the X-ray beam, and during the irradiating, an intensity measurement of the test object appropriately resolved according to the plurality of different energy intervals is carried out by the X-ray measuring facility;
   determining an absorption function of the test object using the intensity measurement of the test object;
   preparing one of the energy intervals as a reference interval such that the absorption function has a negligible energy dependency over the reference interval;
   determining a correction function of the absorption function, for at least one further energy interval of the plurality of different energy intervals, using at least one value of the absorption function in the reference interval; and
   calibrating the X-ray measuring facility using the correction function determined.

2. The method of claim 1, wherein a broadband energy interval is prepared as a reference interval, a lower limit of the broadband energy interval being at least a value of 60% of a maximum energy of a spectrum of the X-ray beam.

3. The method of claim 2, wherein an energy interval provided for energy-resolved normal operation of the X-ray measuring facility is selected as the reference interval.

4. The method of claim 1, wherein a narrowband energy interval is prepared as the reference interval, a spectral width of the narrowband energy interval being at most ⅛ of a maximum energy of a spectrum of the X-ray beam.

5. The method of claim 4, wherein preparation of the reference interval is suspended for energy-resolved normal operation of the X-ray measuring facility.

6. The method of claim 1, further comprising:
   plotting spatially resolved values of the absorption function for the reference interval against values of the absorption function for the at least one further energy interval, and
   determining, from the plotting, the absorption function for the reference interval in a relevant energy interval, depending on the absorption function for the at least one further energy interval, as a correction function.

7. The method of claim 1, wherein the X-ray measuring facility carries out a rotational movement, in respect of the test object, for the intensity measurement of the test object.

8. The method of claim 1, wherein a quantum-counting X-ray detector is calibrated as the X-ray measuring facility.

9. The method of claim 1, wherein the reference interval is prepared over at least one voltage level in a signal amplifier of the X-ray measuring facility.

10. An imaging medical device, comprising:
    at least one X-ray source to generate an X-ray beam; and an X-ray measuring facility, the X-ray measuring facility being configured to be calibrated by preparing the X-ray measuring facility for measurement for a resolution of a plurality of different energy intervals;

positioning a test object in a beam path of an X-ray beam;

irradiating the test object via the X-ray beam, and during the irradiating, an intensity measurement of the test object appropriately resolved according to the plurality of different energy intervals is carried out by the X-ray measuring facility;

determining an absorption function of the test object using the intensity measurement of the test object;

preparing one of the plurality of different energy intervals as a reference interval such that the absorption function has a negligible energy dependency over the reference interval;

determining a correction function of the absorption function, for at least one further energy interval of the plurality of different energy intervals, using at least one value of the absorption function in the reference interval; and calibrating the X-ray measuring facility using the correction function determined.

11. The imaging medical device of claim 10, designed as a computer tomograph.

12. The imaging medical device of claim 10, designed as a C-arm device.

13. The method of claim 2, wherein a narrowband energy interval is prepared as the reference interval, a spectral width of the narrowband energy interval being at most ⅛ of a maximum energy of a spectrum of the X-ray beam.

14. The method of claim 13, wherein preparation of the reference interval is suspended for energy-resolved normal operation of the X-ray measuring facility.

15. The method of claim 2, further comprising:

plotting spatially resolved values of the absorption function for the reference interval against values of the absorption function for the at least one further energy interval, and determining, from the plotting, the absorption function for the reference interval in a relevant energy interval, depending on the absorption function for the at least one further energy interval, as a correction function.

16. The method of claim 2, wherein the X-ray measuring facility carries out a rotational movement, in respect of the test object, for the intensity measurement of the test object.

17. The method of claim 2, wherein a quantum-counting X-ray detector is calibrated as the X-ray measuring facility.

18. The method of claim 2, wherein the reference interval is prepared over at least one voltage level in a signal amplifier of the X-ray measuring facility.

* * * * *